(12) United States Patent
Michalowicz (10) Patent No.: US 7,364,581 B2
(45) Date of Patent: Apr. 29, 2008

(54) VARIABLE ANGLE CUTTING BLOCK

(75) Inventor: Joseph John Michalowicz, Saddle Brook, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 179 days.

(21) Appl. No.: 10/757,619

(22) Filed: Jan. 14, 2004

(65) Prior Publication Data

US 2005/0154394 A1    Jul. 14, 2005

(51) Int. Cl.
*A61F 5/00* (2006.01)
(52) U.S. Cl. ..................................................... 606/87
(58) Field of Classification Search ................. 606/86, 606/87, 88, 89, 79, 80–82, 96, 98, 102, 104
See application file for complete search history.

(56) References Cited

U.S. PATENT DOCUMENTS

| | | | |
|---|---|---|---|
| 2,823,709 A * | 2/1958 | Konieczka ................... 83/745 |
| 4,020,929 A * | 5/1977 | Goldin ................... 188/321.11 |
| 4,608,898 A * | 9/1986 | Volk ............................. 83/745 |
| 4,703,751 A * | 11/1987 | Pohl ............................. 606/62 |
| 5,228,459 A | 7/1993 | Caspari et al. |
| 5,275,603 A * | 1/1994 | Ferrante et al. ................ 606/86 |
| 5,342,367 A | 8/1994 | Ferrante et al. |
| 5,454,816 A | 10/1995 | Ashby |
| 5,484,446 A * | 1/1996 | Burke et al. ................... 606/87 |
| 5,611,353 A | 3/1997 | Dance et al. |
| 5,653,714 A | 8/1997 | Dietz et al. |
| 5,688,280 A | 11/1997 | Booth, Jr. et al. |
| 5,704,941 A | 1/1998 | Jacober et al. |
| 5,788,700 A | 8/1998 | Morawa et al. |
| 5,916,219 A | 6/1999 | Matsuno et al. |
| 6,007,535 A * | 12/1999 | Rayhack et al. ............... 606/57 |
| 6,013,081 A | 1/2000 | Burkinshaw et al. |
| 6,090,114 A | 7/2000 | Matsuno et al. |
| 6,290,704 B1 | 9/2001 | Burkinshaw et al. |
| 6,385,475 B1 | 5/2002 | Cinquin et al. |
| 6,458,135 B1 | 10/2002 | Harwin et al. |
| 6,796,986 B2 * | 9/2004 | Duffner ........................ 606/87 |
| 2002/0156479 A1 | 10/2002 | Schulzki et al. |
| 2002/0198531 A1 | 12/2002 | Millard et al. |
| 2005/0049603 A1* | 3/2005 | Calton et al. .................. 606/87 |
| 2005/0070909 A1* | 3/2005 | Egger et al. ................... 606/87 |

* cited by examiner

*Primary Examiner*—William H. Matthews
(74) *Attorney, Agent, or Firm*—Lerner, David, Littenberg, Krumholz & Mentlik, LLP (57) ABSTRACT

A variable angle cutting block and method for resection a bone are disclosed. The variable angle cutting block comprises a first portion, a second portion, and an angle adjustment system for positioning the first and second portions at a relative angular position upon rotation of the second portion with respect to the first portion. The present invention is useful in allowing for realignment of a cutting guide surface so that a bone cut can be made at a proper varus/valgus angle.

39 Claims, 5 Drawing Sheets

VARIABLE ANGLE CUTTING BLOCK

FIELD OF THE INVENTION

The present invention relates to an apparatus and method for resecting a bone surface, and more particularly, to an apparatus and method for resecting the proximal end of the tibia during a total knee arthroplasty.

BACKGROUND OF THE INVENTION

As with any successful total knee arthroplasty, proper balancing of the knee joint is of the utmost importance. This balancing is achieved primarily through proper distal femoral and proximal tibia resections or cuts, and to a lesser extent, soft tissue release surrounding the joint capsule.

In order to produce accurate distal femoral and proximal tibial cuts, surgeons use various forms of cutting blocks. The cutting blocks, as useful a tool as they are, still need to be properly positioned by the surgeon. Once properly positioned, the cutting block is fixed to the bone so that a cutting guide surface, usually a saw guide surface, is in correct alignment for performing the required bone resection. However, occasionally after the block is fixed to bone, the surgeon realizes that the cutting guide surface needs to be realigned. To do this, the surgeon must remove the block from the bone and re-attach it in the correct position. Thus there has been a need for ways to reposition the cutting guide surface without removing the entire block from the bone.

U.S. Pat. No. 4,703,751 to Pohl, relates to a distal femoral resection guide having two plates, wherein one plate is positioned on the femur surface and the second plate is positioned on the first plate. Rotational movement is allowed between the first and second plates, and the second plate can be fixed to the first plate by a screw.

U.S. Patent Application Publication No. 2002/0198531 to Millard et al., relates to an apparatus for positioning the cutting angle of a bone cutting guide. The cutting guide is fixed to the bone surface upon determination of the proper angle.

U.S. Pat. No. 5,342,367 to Ferrante et al., relates to a cutting guide for ostectomy of the medial and lateral tibial surface during knee surgery.

U.S. Pat. No. 6,090,114 to Matsuno et al., relates to an apparatus for resecting the tibia. Stabilizing pins are placed in the cutting block, upon proper alignment, thereby allowing the proper tibial plateau resection plane to be created.

As mentioned above, the position of the cutting block needs to be determined by the surgeon, and one of the position determinations, in total knee arthroplasty, relates to the varus/valgus angle. Varus refers to rotation inward towards the midline of the body; while, valgus refers to rotation away from the midline of the body. This angle must be determined prior to making the proximal tibial cut, as an improper angle will prevent proper balancing of the knee joint. A cutting block placed on the anterior side of the proximal tibia, would need to be properly positioned according to the varus/valgus angle, i.e., rotated in a clockwise or counterclockwise fashion about an anterior-posterior axis through the proximal tibia.

Typically, when a surgeon positions a proximal tibial cutting block and realizes that the cutting guide surface is incorrectly positioned, i.e., at the wrong varus/valgus angle, he has several options, if a resection has already been made. One option is that a free hand cut with a sagital saw can be made, at, for example, a corrected varus/valgus angle, but this process does not often provide a perfectly accurate cut. Alternatively, the surgeon may simply accept the error and attempt to compensate in some other manner. In another option, the tibial cutting block originally fixed in an incorrect position and utilized to make an original cut, can be repositioned and re-pinned at a new varus/valgus angle. Finally, a correction block having a different varus/valgus angle can be slid over the existing pins used for the original cutting block. However, all of these options create additional work for a surgeon and add time to an already extensive surgery. Therefore, there is a need for a cutting block that can allow for resection at various varus/valgus angles, without having to be repositioned and re-fixed or re-pinned to the bone.

SUMMARY OF THE INVENTION

An adjustable bone resection guide is provided having a first portion having a surface adjacent a bone surface able to be fixed with respect to a bone surface. The guide has a second portion rotatably coupled to the first portion including a bone resection guide surface and a surface adjacent a bone surface. A position means is provided for positioning the first and second portions at a relative angular position upon rotation of the second portion about the pivot point, the means for positioning being spaced apart from the pivot point.

A bone resection guide comprising a first portion having a surface adjacent a bone surface, a second portion having a bone resection guide surface and a surface adjacent a bone surface thereon, the second portion pivotably couple to the first portion at a pivot point, and an angle adjustment element mounted on the first portion and engageable with the second portion, for setting the angular position of the second portion with respect to the first portion about the pivot point, the angle adjustment element being spaced apart from the pivot point.

A bone resection guide comprising a first portion having a first and second ends and a surface adjacent a bone surface, a second portion having a bone resection guide surface and a surface adjacent a bone surface thereon, the second portion pivotably coupled to said first portion at a pivot point adjacent the first ends of the first and second portions, and an angle adjustment element mounted on the second end of the first portion and engageable with the second portion, for setting the angular position of the second portion with respect to the first portion about the pivot point.

The invention includes a method of resecting a bone using the guide by providing the adjustable bone resection guide having a first portion rotatably couple to a second portion, wherein the first and second portions have surfaces adjacent a bone surface. The angle is determined and the guide surface on the second portion is positioned at the angle for resection by rotating the second portion with respect to the first portion, fixing the first portion with respect to a bone surface and resecting the bone utilizing a cutting tool and the guide surface.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

In describing the preferred embodiments of the subject matter illustrated and to be described with respect to the drawings, specific terminology will be resorted to for the sake of clarity. However, the invention is not intended to be limited to the specific term so selected, and is to be understood that each specific term includes all technical equivalence which operate in a similar manner to accomplish a similar purpose.

Figure 1:
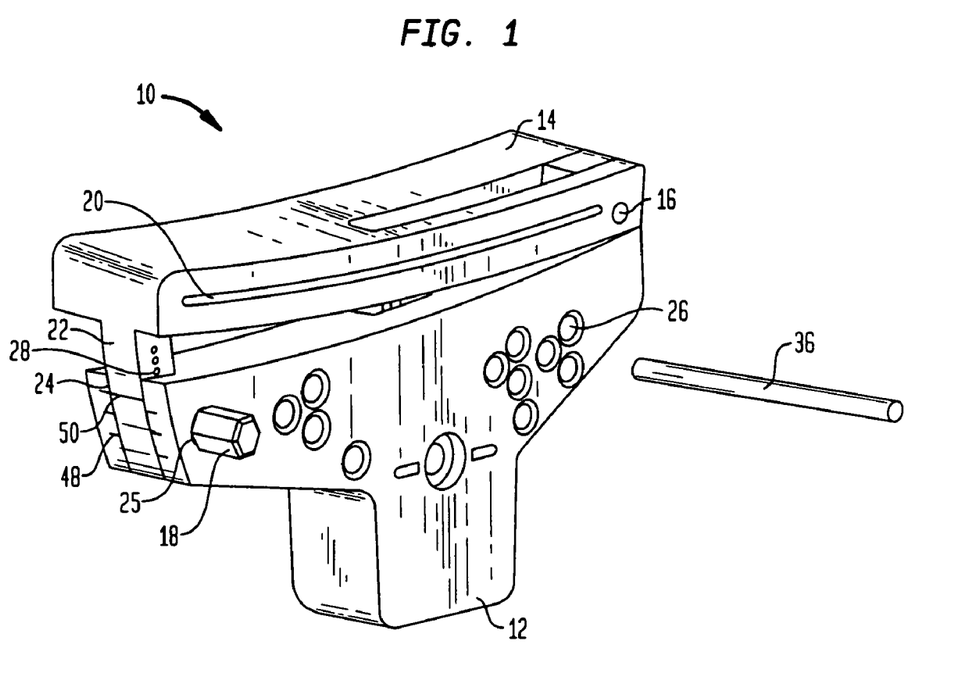
FIG. 1 is a perspective view of the apparatus according to an embodiment of the present invention with the varus/valgus angle set at zero degrees.

Referring to the drawings, wherein like reference numerals represent like elements, there is shown in FIGS. 1-4, in accordance with a preferred embodiment of the present invention, an adjustable bone resection guide, or variable angle cutting block, designated generally by reference numeral 10. In a preferred embodiment, cutting block 10 includes a first portion 12, a second portion 14, and screw 18. When the cutting block 10 is used on the tibia, second portion 14 is adjacent the proximal tibia. As shown in FIG. 1, first portion 12 and second portion 14 are rotatably attached to one another at pivot point 16. Pivot point 16 allows for the rotation of second portion 14 with respect to first portion 12. In a preferred embodiment, first portion 12 is fixed in relative position with respect to a bone surface while second portion is still able to rotate. However, other embodiments are contemplated that allow for the relative movement of first and second portions 12 and 14. In the illustrated preferred embodiment shown in FIGS. 1-4, pivot point 16 is located at an extreme end of both first and second portions 12 and 14 respectively. However, it should be noted that it is contemplated that pivot point 16 can be located at any position along either portion and need not be located at corresponding positions on each portion. For example, pivot point 16 can be located at a midpoint of first portion 12, while being located at an end of second portion 14 or at a central portion of second portion 14. Other variations are also contemplated. The manner of attachment of first portion 12 to second portion 14 is disclosed more fully below.

Figure 2:
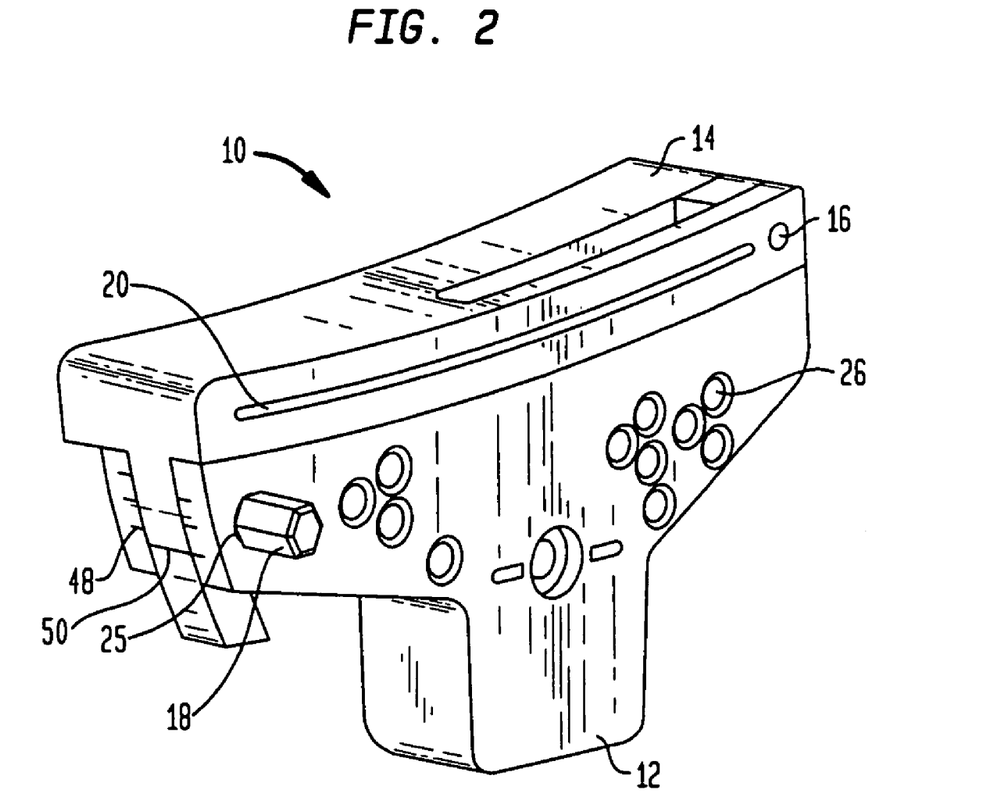
FIG. 2 is a perspective view of the apparatus according to an embodiment of the present invention with the varus/valgus angle set at five degrees varus for use with a left knee arthroplasty.
Figure 3:
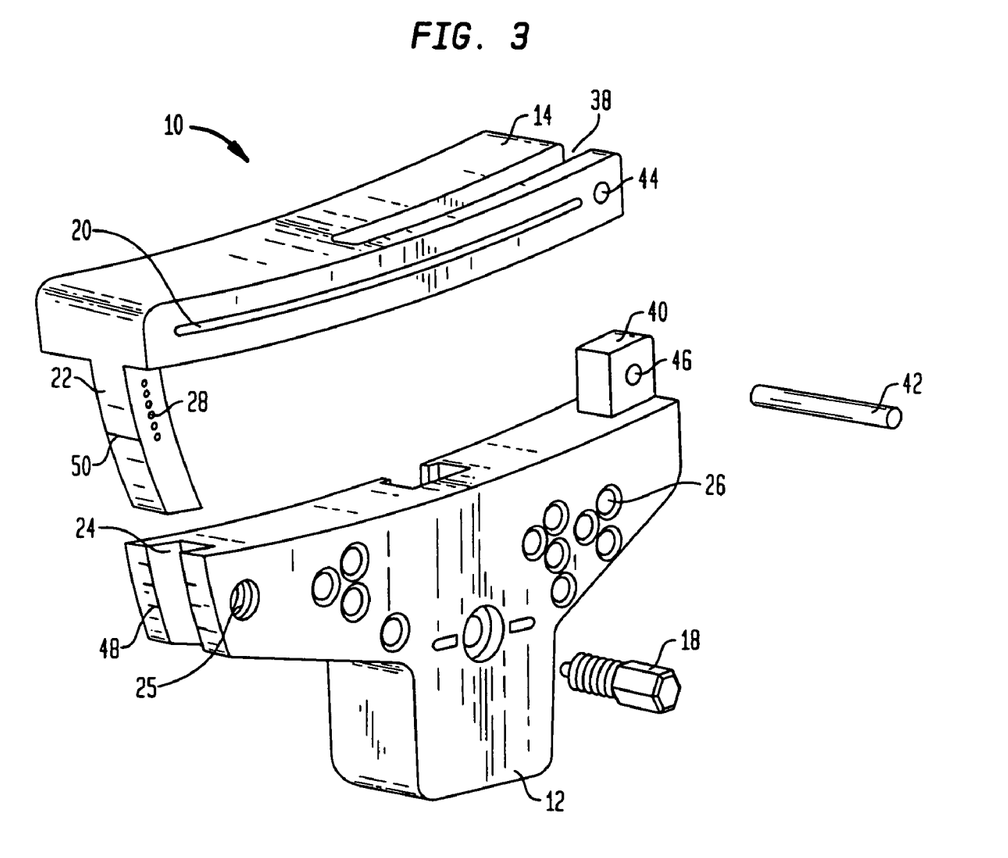
FIG. 3 is an exploded view of the apparatus according to an embodiment of the present invention.
Figure 4:
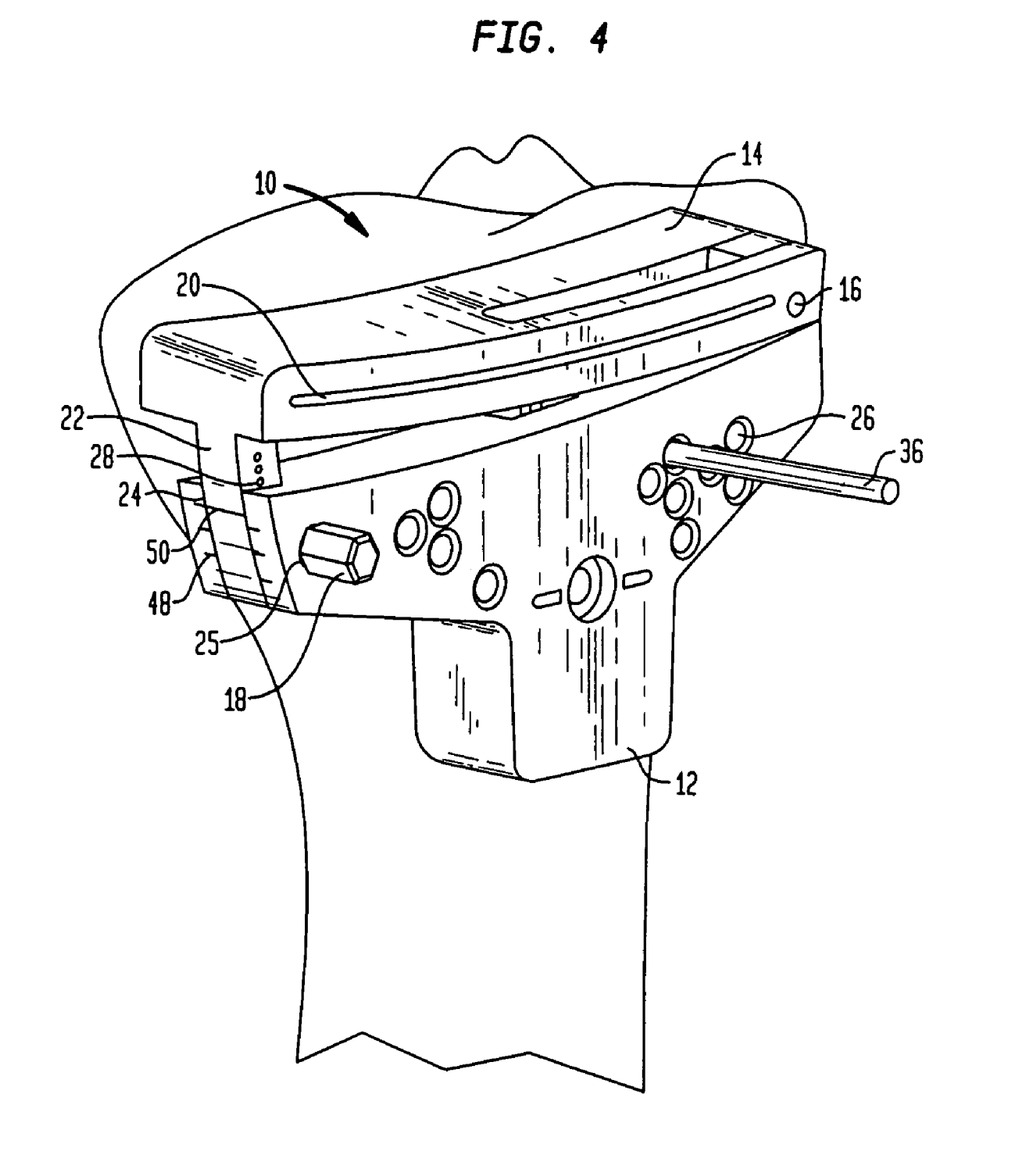
FIG. 4 is a perspective view of the apparatus according to an embodiment of the present invention mounted to the proximal end of a tibia; and, FIG. 5 is an enlarged perspective view of the screw according to an embodiment of the present invention.
Figure 5:
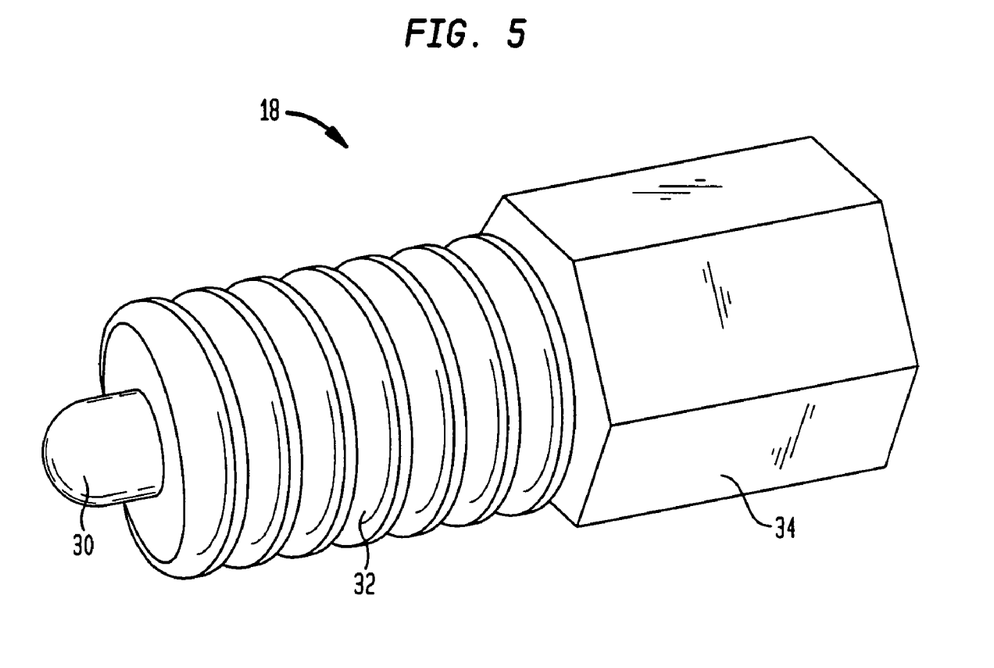

As shown in FIGS. 1-4, in the preferred embodiment, first portion 12 further includes a plurality of apertures 26 for facilitating connection of first portion 12 to a bone surface with pins in a well-known manner (shown in FIG. 4). In the preferred embodiment, at least one pin 36 (shown in FIGS. 1 and 4) is inserted through aperture 26 and into a bone surface. Additional pins may be inserted until the desired connectivity is reached. Similarly, more or fewer apertures 26 may be included on first portion 12, depending upon the need for connectivity. It is contemplated that other modes of fixing first portion 12 with respect to a bone surface can be utilized. In another embodiment, first portion 12 is fixed without the need for pins by utilizing an external support such as, for example, a clamp. First portion 12 also includes a recess or opening 24, as best shown in FIG. 3 (the preferred second portion 14 includes an arm 22 integral herewith). Recess 24 receives arm 22 and aids in the positioning of second portion 14 with respect to first portion 12. Finally, first portion 12 includes a screw hole 25, as shown in FIGS. 1-4. Screw hole 25 houses screw 18 which, in the preferred embodiment, also aids in the positioning of second portion 14 with respect to first portion 12 by engaging arm 22. The operation of screw 18 is discussed in more detail below.

As shown in FIGS. 1-4 second portion 14 further includes a guide surface 20 for receiving and guiding a cutting tool such as a saw blade (not shown). In the preferred embodiment, shown in FIGS. 1-4, the guide surface 20 is a slot. A variety of tools can be received in slot 20 and are prevented from operating outside of the confined area created by slot 20. It is contemplated that guide surface 20 can be of any shape or form allowing for a cutting tool to make precise and accurate cuts. For example, guide surface 20 can be a flat surface as is known in the art. A cutting tool could move along this surface as long as pressure is applied to the cutting tool, preventing it from cutting away from the surface. Additionally, guide surface 20 can be of any shape for facilitating a cut of the same shape. In the preferred embodiment, arm 22 has a plurality of arm holes 28. Arm 22 and holes 28 both aid in the positioning of second portion 14 with respect to first portion 12.

In a preferred embodiment, as shown in FIGS. 1-5 (most notably in FIG. 5) screw 18 further includes dimple 30, thread 32, and head 34 for a driver. The preferred head 34 has a hex shape. However, it is contemplated that any type of drive head for use with a corresponding type of driver tool can be utilized. Thread 32 can be any type but preferably is a helical thread. Finally, dimple 30 is a protrusion extending from the end of thread 32. In a preferred embodiment, screw 18 is housed in a threaded screw hole 25 of first portion 12. As best seen in FIG. 3, screw hole 25 extends through first portion 12 so that screw 18 can access recess 24. This allows for dimple 30 to contact at least one arm hole 28 located on arm 22. Upon insertion of dimple 30 into arm hole 28 of arm 22, second portion 14 is locked into place with respect to first portion 12, i.e., second portion 14 can no longer rotate about pivot point 16 with respect to first portion 12. Screw hole 25 allows for the selective advancement of screw 18 therein, allowing for dimple 30 to engage and to remain in contact with arm hole 28 or be withdrawn from hole 28. In use, head 34 of screw 18 is rotated to allow for insertion or removal of dimple 30 into or out of arm hole 28. The direction or rotation is determined by the thread type.

It is contemplated that the mode of positioning second portion 14 with respect to first portion 12 can be accomplished by other structures than those disclosed above. For example, a pin or other elongated object can be utilized in place of screw 18 and arm holes 28 can be of any shape and/or size. It is contemplated that arm 22, recess 24, and screw hole 25 can be located at various positions along first and second portions 12 and 14. For example, recess 24 and screw hole 25 could be located at the midpoint of first portion 12, while arm 22 could be located at a corresponding midpoint of second portion 14. In another embodiment, a locking mechanism located at pivot point 16 can be employed. This locking mechanism locks into position as the second portion 14 is rotated in either direction. A typical design would have a spring-loaded dimple that when depressed allows for rotational movement of second portion 14, but when not depressed springs back and extends into a recess, thereby preventing rotational movement. However, other forms of engagement and locking can be used to achieve the same benefits of a pivoting guide surface. In yet another embodiment, arm 22 can be located on first portion 12 and recess 24 and screw 18 can be located on second portion 14. In some embodiments, cutting block 10 may further include a scale or measurement device for aiding in the determination of the proper angle of resection, therefore simplifying the positioning of second portion 14 with respect to first portion 12. In the preferred embodiment, angle markings 48 at 2, 4, 6, and 8 degree increments (FIGS. 1-4) and reference mark 50 (FIG. 3) are utilized to set this angle.

In a preferred embodiment, as shown in FIG. 3, the pivot is in the form of a hinge having a pivot slot 38, pivot body 40, and pivot pin 42. Pivot slot 38 further includes a pivot pin hole 44 and pivot body 40 further includes pivot pin hole 46. Pivot slot 38 is sized so as to fit pivot body 40 and allow the relative movement there between. Upon insertion of pivot body 40 into pivot slot 38, pivot pin hole 44 and pivot pin hole 46 align so as to create one long bore extending through both first portion 12 and second portion 14. Pivot pin 42 is inserted through pivot pin hole 46 and through pivot pin hole 44, thereby creating a hinge allowing for second portion 14 to rotate with respect to first portion 12. It should be noted that other modes of attaching first portion 12 to second portion 14 are contemplated. For example, in another embodiment, a separate hinge apparatus can be utilized and connected to the first and second portions 12 and 14, at the ends of each portion. A hinge of this type is well known in the art, and can best be described as of the type utilized on standard doors. Similarly, as mentioned above, pivot point 16 can be located at any position along either first portion 12 or second portion 14. For example, in one embodiment, pivot point 16 can be located at the midpoint of both first and second portions 12 and 14. This embodiment is a fulcrum (much like in a seesaw) wherein a locking structure is provided so that second portion 14 can be locked in position on either side of the pivot point 16.

A method of resecting, or cutting, a bone will now be described in connection with the tibia, as part of a total knee arthroplasty. However, it should be noted that the present invention has general applicability to various bones and bone resecting procedures. For example, the present invention can be utilized for making a cut on the distal end of the femur. However, other embodiments are contemplated for resecting other bones in other areas of the body.

As stated above, the preferred method of the present invention is performed on the proximal end of the tibia, during a total knee arthroplasty. During surgery, second portion 14 is initially set and fixed to a zero degree resection angle, with respect to the first portion 12 (shown in FIG. 1). This is accomplished by utilizing angle markings 48 and reference mark 50, or any other suitable aids on cutting block 10, which allow for easy positioning of second portion 14 and more importantly, guide surface 20. In the preferred embodiment, reference mark 50 is lined up with the corresponding angle marking 48, relating to the determined angle (in this case, zero degrees). To facilitate fixing the second portion 14 with respect to the first portion 12, screw 18 is placed in screw hole 25. A standard tool is utilized to turn screw 18 in order to engage dimple 30 with the correct arm hole 28, corresponding to the desired angular position (zero degrees) of second portion 14 with respect to first portion 12. Upon full insertion, screw 18 seats in hole 28 and can no longer turn in screw hole 25.

After fixing second portion 14 with respect to first portion 12, the proper varus/valgus angle for resection must be determined. The initial setting and fixing of second portion 14 with respect to first portion 12, allows for the entire cutting block 10 to be aligned on the proximal tibia at the proper resection angle, according to any procedure typically utilized on a cutting block. There are many well known methods for determining the proper varus/valgus angle in the prior art. For example, U.S. Pat. No. 5,916,219 to Matsuno et al. (hereby incorporated by reference) discloses an apparatus and method for tibial alignment which allows the independent establishment of two separate geometric planes to be used as a reference for the cutting of the tibial plateau during total knee arthroplasty. Other methods are shown in U.S. Pat. No. 5,704,941 to Jacober et al., U.S. Pat. No. 5,788,700 to Morawa et al., and U.S. Pat. No. 6,090,114 to Matsuno et al. Furthermore, a navigation tracker may be attached to the cutting guide 10 and/or second portion 14 for initial and final placement/orientation of the cutting guide 10 and cutting surface 20. For example, an optical tracker is shown in U.S. Pat. No. 5,611,353 to Dance et al. and U.S. Pat. No. 6,385,475 to Cinquin et al. Cutting block 10 is then placed adjacent the tibia and the lower portion 12 is fixed with respect to the anterior proximal tibia. However, it is also possible for cutting block 10 to be fixed to the medial or lateral sides of the proximal end of the tibia. In the preferred embodiment, the first portion 12 is fixed to the tibia by at least two pins 36 inserted through apertures 26 and into the bone surface. As discussed above, other connections can be employed as well.

Finally, the resection of the proximal tibia is made using a cutting tool, such as a saw, (as is known in the art) and guide surface 20. In the preferred embodiment, guide surface 20 is a slot and a saw blade is guided therein. Upon completion of the resection of the tibia, the surgeon then removes cutting block 10, while any pins 36 remain in the bone. This is accomplished by sliding first portion 12 away from the bone surface, thereby allowing pins 36 to remain in the bone material and the alignment of the resected tibia to be properly verified. If the cut is thereafter determined to be at an improper resection angle or if an adjustment of the angle is required after first portion 12 is attached before the initial resection, second portion 14 and guide surface 20 can be repositioned, with respect to first portion 12. This is accomplished by simply backing off or removing screw 18, realigning second portion 14 with respect to first portion 12, and thereafter reinserting or retightening screw 18 as disclosed above. First portion 12 can then be slid back onto pins 36 and a second cut can be made. An example of second portion 14 realigned with respect to first portion 12 is shown in FIG. 2. FIG. 2 is a perspective view of the apparatus according to an embodiment of the present invention with the varus/valgus angle set at five degrees varus for use with a left knee arthroplasty (Note—this same cutting block would be five degrees valgus for a right knee arthroplasty. Typically, two blocks will be provided, one being the mirror image of another.)

Additionally, the resection level, in the proximal/distal direction, may also be adjusted by sliding the guide onto pins 36 utilizing a different level of apertures 26 on first portion 12. In another embodiment, cutting block 10 can remain on the bone surface, while second portion 14 is repositioned with respect to first portion 12. Finally, in cases where pins 36 are not used, the cutting block 10 can either remain fixed in relative position with the bone surface, or be removed in another fashion. For example, in the cases where the cutting block 10 is fixed through the use of some external structure. At the completion of the cut, at the proper resection angle, cutting block 10 and any pins 36 can be removed from the bone surface.

In another embodiment, cutting block 10 is initially placed adjacent the proximal end of the tibia on any one of the anterior, medial, or lateral sides. The first portion 12 is then aligned and fixed with respect to the bone surface, by any means disclosed above. After fixing first portion 12, the proper varus/valgus angle is determined according to any method as disclosed above. Upon determination of the proper resection angle, second portion 14 is aligned and fixed with respect to first portion 12 (also discussed above). Finally, the resection of the proximal tibia is made using a cutting tool, such as a saw (as is known in the art) and guide surface 20. If the cut is thereafter determined to be at an improper resection angle or if an adjustment of the angle is required after first portion 12 is attached before the resection, second portion 14 and guide surface 20 can be repositioned, with or without first portion 12 remaining fixed with respect to the bone surface. The method of repositioning second portion 14 is disclosed above. It is also contemplated that the steps in the above disclosed methods can be performed in any order able to complete the function of cutting the bone at the proper resection angle. It should be noted that in the situation where the cutting block 10 is mounted on the medial or lateral side of the tibia, the angular adjustment of second portion 14 with respect to first portion 12 would determine the slope of the tibial cut or flexion/extension. In other words, the angular adjustment of second portion 14 with respect to first portion 12 would tilt the cut forward or backward in the anterior-posterior direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adjustable bone resection guide comprising:
   a. a first portion adapted to be fixed with respect to a bone surface, said first portion having:
      i. a surface adapted to be located adjacent said bone surface and;
      ii. a plurality of bone fastener receiving apertures, the bone fastener receiving apertures arranged in at least two vertically spaced rows each said row including two or more of said bone fastener receiving apertures;
   b. a second portion rotatably coupled to said first portion at a pivot point thereon, said second portion having:
      i. a bone resection guide surface, said guide surface formed by a slot and;
      ii. a surface adapted to be located adjacent said bone surface; and,
   c. means for positioning said first and second portions at a relative angular position upon rotation of said second portion about said pivot point, said means for positioning being spaced apart from said pivot point; wherein said resection guide is used in guiding a bone resecting tool, wherein both said surfaces adapted to be located adjacent said bone surface extend along a first plane and said slot and said bone fastener receiving apertures extend perpendicularly to said first plane.

2. The adjustable bone resection guide of claim 1, further including at least one bone fastener for connecting said first portion to said bone surface.

3. The adjustable bone resection guide of claim 2, wherein said second portion can be rotated without said first portion being removed from said bone surface while said first portion is connected to said bone surface.

4. The adjustable bone resection guide of claim 1, wherein one of said first or second portions further comprises a recess and the other of said first or second portions further comprises an arm, wherein said arm is received within said recess.

5. The adjustable bone resection guide of claim 4, wherein said means for positioning said second portion with respect to said first portion includes a screw mounted to both the first and second portions.

6. The adjustable bone resection guide of claim 5, wherein said arm further comprises at least one hole.

7. The adjustable bone resection guide of claim 6, wherein said screw further comprises a dimple on a first end, wherein said dimple locks into one of said at least one hole on said arm.

8. The adjustable bone resection guide of claim 2, wherein said at least one bone fastener is selected from the group consisting of pins, wires, screws and nails.

9. The adjustable bone resection guide of claim 8, wherein said guide includes a plurality of apertures and a plurality of bone fasteners in said apertures.

10. The adjustable bone resection guide of claim 1, wherein said adjustable bone resection guide is a tibial resection guide.

11. The adjustable bone resection guide of claim 1, wherein angular movement of said second portion with respect to said first portion allows for varying varus/valgus angles.

12. A bone resection guide comprising:
   a. a first portion having:
      i. a surface adapted to be located adjacent a bone surface and;
      ii. a plurality of bone fastener receiving apertures, the bone fastener receiving apertures arranged in at least two vertically spaced rows each said row including two or more of said bone fastener receiving apertures;
   b. a second portion pivotably coupled to said first portion at a pivot point, said second portion having:
      i. a bone resection guide surface, said guide surface formed by a slot and;
      ii. a surface adapted to be located adjacent said bone surface thereon; and,
   c. an angle adjustment element mounted on said first portion and engageable with said second portion, for setting the angular position of said second portion with respect to said first portion about said pivot point, said angle adjustment element being spaced apart from said pivot point; wherein said resection guide is used in guiding a bone resecting tool, wherein both said surfaces adapted to be located adjacent said bone surface extend along a first plane and said slot and said bone fastener receiving apertures extend perpendicularly to said first plane.

13. The bone resection guide of claim 12, wherein said angle adjustment element further includes a locking element extending between said angle adjustment element and one of said first and second portions.

14. The bone resection guide of claim 12, wherein said first portion is able to be fixed with respect to a bone surface.

15. The bone resection guide of claim 14, further including a bone fastener for connecting said first portion to said bone surface.

16. The bone resection guide of claim 15, wherein said second portion can be rotated without said first portion being removed from said bone surface while said first portion is connected to said bone surface.

17. The bone resection guide of claim 15, wherein said bone fastener is selected from the group consisting of pins, wires, screws and nails.

18. The bone resection guide of claim 17, wherein said guide includes a plurality of apertures and a plurality of bone fasteners in said apertures.

19. The bone resection guide of claim 12, wherein said angle adjustment element further comprises a recess on one of said first or second portions and an arm on the other of said first or second portions, wherein said arm is received within said recess.

20. The bone resection guide of claim 19, wherein said angle adjustment element further comprises a screw mounted to both the first and second portions.

21. The bone resection guide of claim 20, wherein said arm further comprises at least one hole.

22. The bone resection guide of claim 21, wherein said screw further comprises a dimple on a first end, wherein said dimple locks into one of said at least one hole on said arm.

23. The bone resection guide of claim 12, wherein said bone resection guide is a tibial resection guide.

24. The bone resection guide of claim 12, wherein said angular position of said second portion with respect to said first portion relates to a varus/valgus angle.

25. A bone resection guide comprising:
  a. a first portion having a first and second ends, a surface adapted to be located adjacent a bone surface, and a plurality of bone fastener receiving apertures, the bone fastener receiving apertures arranged in at least two vertically spaced rows each said row including two or more of said bone fastener receiving apertures;
  b. a second portion having a slotted bone resection guide surface and a surface adapted to be located adjacent said bone surface thereon, said second portion pivotably coupled to said first portion at a pivot point adjacent said first ends of said first and second portions; and,
  c. an angle adjustment element mounted on said second end of said first portion and engageable with said second portion, for setting the angular position of said second portion with respect to said first portion about said pivot point; wherein said resection guide is used in guiding a bone resecting tool, wherein both said surfaces adapted to be located adjacent said bone surface extend along a first plane and said slot and said bone fastener receiving apertures extend perpendicularly to said first plane.

26. The bone resection guide of claim 25, wherein said angle adjustment element further includes a locking element extending between said angle adjustment element and one of said first and second portions.

27. The bone resection guide of claim 25, wherein said first portion is able to be fixed with respect to a bone surface.

28. The bone resection guide of claim 27, further including a bone fastener for connecting said first portion to said bone surface.

29. The bone resection guide of claim 28, wherein said second portion can be rotated without said first portion being removed from said bone surface while said first portion is connected to said bone surface.

30. The bone resection guide of claim 28, wherein said bone fastener is selected from the group consisting of pins, wires, screws and nails.

31. The bone resection guide of claim 30, wherein said guide includes a plurality of apertures and a plurality of bone fasteners in said apertures.

32. The bone resection guide of claim 25, wherein said angle adjustment element further comprises a recess on one of said first or second portions and an arm on the other of said first or second portions, wherein said arm is receive within said recess.

33. The bone resection guide of claim 32, wherein said angle adjustment element further comprises a screw mounted to both the first and second portions.

34. The bone resection guide of claim 33, wherein said arm further comprises at least one hole.

35. The bone resection guide of claim 34, wherein said screw further comprises a dimple on a first end, wherein said dimple locks into one of said at least one hole on said arm.

36. The bone resection guide of claim 25, wherein said bone resection surface is planar.

37. The bone resection guide of claim 36, wherein said first and second portions pivot about an axis extending parallel to said plane.

38. The bone resection guide of claim 25, wherein said bone resection guide is a tibial resection guide.

39. The bone resection guide of claim 25, wherein said angular position of said second portion with respect to said first portion relates to a varus/valgus angle.

* * * * *